United States Patent
Culver et al.

(10) Patent No.: US 6,487,428 B1
(45) Date of Patent: Nov. 26, 2002

(54) EXTRAVASATION DETECTION APPARATUS AND METHOD BASED ON OPTICAL SENSING

(75) Inventors: Joseph P. Culver, Philadelphia, PA (US); Arjun G. Yodh, Merion, PA (US)

(73) Assignee: Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/652,757

(22) Filed: Aug. 31, 2000

(51) Int. Cl.$^7$ ................................................. A61B 5/00
(52) U.S. Cl. ......................... 600/310; 600/309; 600/475
(58) Field of Search .................................. 600/309–310, 600/335, 454, 473, 474, 476, 475; 604/290, 500–512

(56) References Cited

U.S. PATENT DOCUMENTS

| | | | | |
|---|---|---|---|---|
| 4,647,281 A | * | 3/1987 | Carr ............................. | 604/503 |
| 4,877,034 A | * | 10/1989 | Atkins et al. ................ | 600/475 |
| 5,435,309 A | * | 7/1995 | Thomas et al. .............. | 600/310 |
| 5,947,910 A | * | 9/1999 | Zimmet ........................ | 600/547 |
| 5,954,668 A | * | 9/1999 | Uber, III et al. ............. | 600/549 |

FOREIGN PATENT DOCUMENTS

| | | | | |
|---|---|---|---|---|
| WO | WO 99/15074 | * | 4/1999 | ............ A61B/5/00 |

OTHER PUBLICATIONS

Siegel A.M., Marota, J.J.A., Boas D.A., "Design and evaluation of a continuous–wave diffuse optical Tomography system", Optical Express, $: (8) 287–298 Apr. 12, 1999.

"Optimum Signal Processing", An Introduction, S.J. Orfanidis, McGraw–Hill, 1988, section "correlation canceling", pp. 9–15.

O'Leary M.A., Boas D.A., Change B., Yodh A.G., "Experimental images of heterogeneous turbic media by frequency–domain diffusin –photon tomography" Optics Letters, 20: (5) 426–428 Mar. 1, 1995.

Arridge S.R., "Optical tomography in medical imaging" *Inverse Problems*, 15 (1999) R41–R93.

* cited by examiner

*Primary Examiner*—Kevin Shaver
*Assistant Examiner*—Matthew Kremer
(74) *Attorney, Agent, or Firm*—RatnerPrestia

(57) ABSTRACT

Extravasation of a fluid applied to a patient is determined by monitoring light transmitted through the tissue of the patient in proximity to a site at which the fluid is being injected. Light is radiated from a plurality of light sources in an encoded manner into the body part at the site at which the fluid is injected and the light that is reflected, scattered, diffused or otherwise emitted from the body part is detected individually by a plurality of light detectors. Signals representative of the detected light are developed and, prior to injection of the fluid, references are developed against which measurements made during injection of the fluid are compared. New light signals having an improved signal-to-noise ratio are developed from the comparisons of the detected light signals with the associated reference signals. Prior to injection of the fluid into the body part, a model, dependent on the arrangement of the light sources and the light detectors on the support pad is developed for calculating extravasation volume from the new light signals having an is improved signal-to-noise ratio. The new light signals having an improved signal-to-noise ratio are combined according to the model to determine the volume of extravasation and the volume of extravasation is compared with a prescribed level of extravasation.

17 Claims, 7 Drawing Sheets

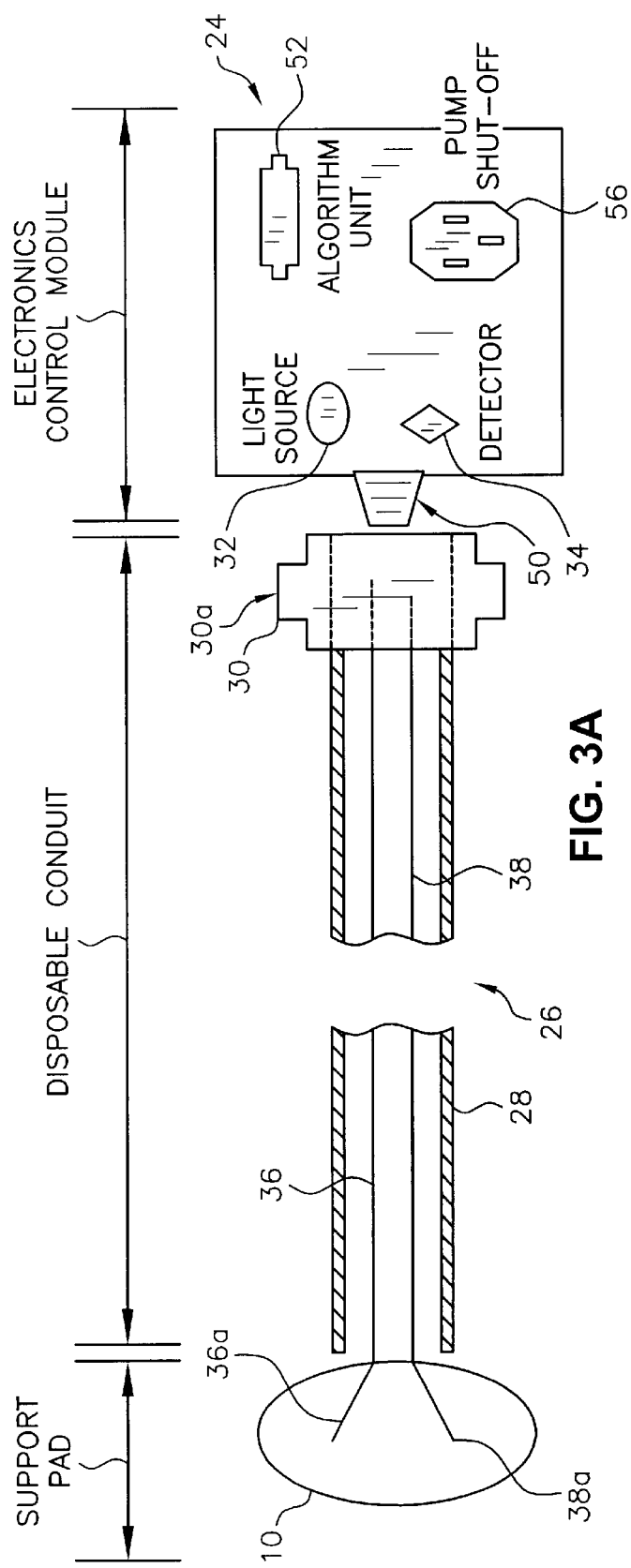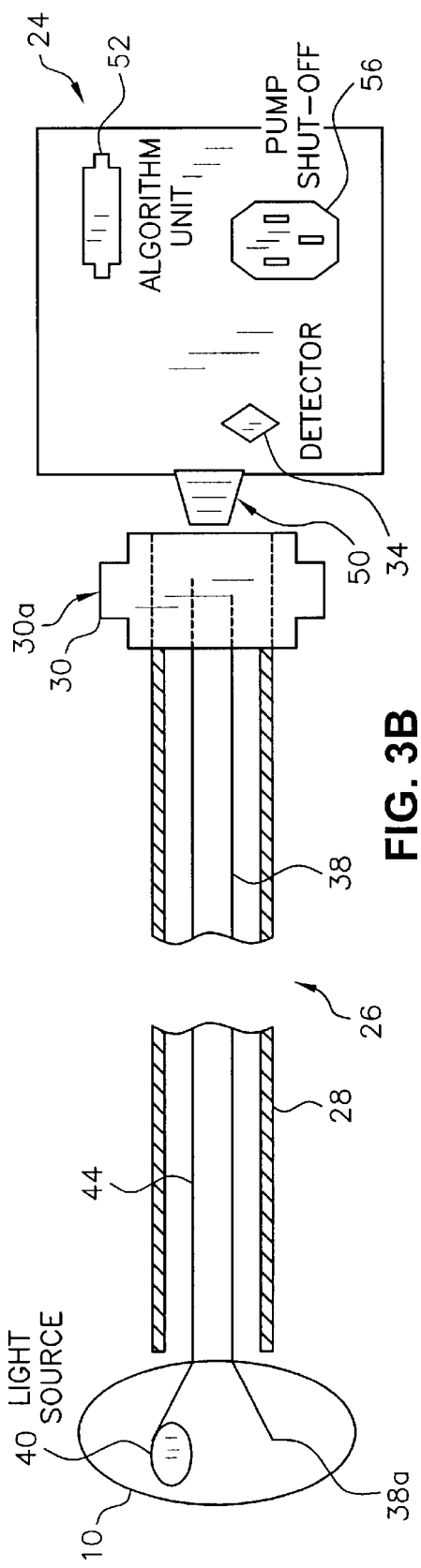

EXTRAVASATION DETECTION APPARATUS AND METHOD BASED ON OPTICAL SENSING

TECHNICAL FIELD

The present invention relates, in general, to the detection of extravasation (i.e. leakage) of infusions and the like and, in particular, to optically detecting extravasation at an infusion site.

BACKGROUND OF THE INVENTION

Various beneficial substances are intravascularily administered to hospital patients. Examples of these substances are fluids such as contrast media, medicinal fluids, water, electrolytes, sugar, blood, and pharmaceuticals. These substances typically are administered with a needle that is adapted to be inserted into an appropriate vein or artery.

Extravasation occurs when, during the infusion of such a substance, the substance being applied infiltrates the area around the vein or artery. For example, improper insertion of a needle or movement of the patient can cause the needle to pierce the far vascular wall so that the substance is administered into the perivascular tissue or the needle can simply withdraw from the vein or artery and inadvertently inject fluid into the surrounding tissue.

Extravasation can occur while using a variety of units that are used to inject fluids into a patient. Such units include, for example, syringes, power injectors, intravascular drips, intravascular pumps and the like.

Among the various injected substances are diagnostic contrast agents and chemotherapy substances that can be toxic or irritating to body tissue. The extravasation of such substances and others can cause serious harm to patients. Consequently, immediate and accurate detection of extravasation can be very important with such toxic substances, as well as with other injected substances. There is a particularly high risk of injury when high speed bolus injections are used with various medical imaging contrast agents.

A variety of methods for extravasation detection are known in the art.

U.S. Pat. No. 4,647,281 describes and illustrates and infiltration detection apparatus that utilizes microwave antenna means positioned over an area of infusion and a microwave radiometer for detecting sub-cutaneous temperature. Extravasation is detected by temperature differentials between injected fluids and surrounding tissues.

U.S. Pat. No. 5,334,141 describes and illustrates another system for extravasation detection that also monitors electromagnetic microwave emissions from the patient. This patent shows an antenna assembly having a reusable antenna element connected to processing apparatus and a disposable attachment element for adhering to the skin of a patient.

U.S. Pat. No. 4,877,034 describes and illustrates yet another non-invasive system that allows detection of tissue infiltration during the administration of fluids. Tissue surrounding the site of intravenous injection is exposed to a plurality of wavelengths of electromagnetic radiation when no infiltration is occurring to determine a baseline reading. Changes in the relative levels of detected radiation at each wavelength as compared to the baseline reading indicate tissue infiltration.

Another technique previously suggested involves use of an optical device that detects extravavsation and subsequently controls the injector to stop further supply of the of the contrast agent. The basic idea underlying this technique requires that, when a light emitter-detector pair is placed proximal to a catheterized vessel, the detected signal dynamics will differentiate extravasations from in vessel injections.

SUMMARY OF THE INVENTION

Extravasation detection apparatus, constructed in accordance with the present invention, includes a support pad adapted for attachment to a body part of a patient in proximity to a site at which a fluid is to be injected into the patient and a plurality of light sources, mounted to the support pad, for radiating light into the body part. Also included in this extravasation detection apparatus are means for energizing the light sources in an encoded manner to radiate light into the body part in an encoded manner. Extravasation detection apparatus, constructed in accordance with the present invention, also includes a plurality of light detectors, mounted to the support pad, for individually detecting light transmitted from the light sources that is reflected, scattered, diffused or otherwise emitted from the body part and individually developing light source/light detector pair signals representative of the light detected by the light detectors. Extravasation detection apparatus, constructed in accordance with the present invention, further includes means for developing, prior to injection of the fluid into the body part, a plurality if individual light source/light detector pair baseline signals associated with each light source/light detector pair and against which measurements made during injection of the fluid into the body part are compared and means for comparing the light source/light detector pair signals with the associated light source/light detector pair baseline signals. This extravasation detection apparatus also includes means for developing from the comparisons of the light source/light detector pair signals with the associated light source/light detector pair baseline signals new light source/light detector pair signals having an improved signal-to-noise ratio. Also included in extravasation detection apparatus constructed in accordance with the present invention are means for developing, prior to injection of the fluid into the body part, a model, dependent on the arrangement of the light sources and the light detectors on the support pad, for calculating extravasation volume from the new light source/light detector pair signals having an improved signal-to-noise ratio and means for combining, according to the extravasation model, the new light source/ light detector signals having an improved signal-to-noise ratio to determine the volume of extravasation. This extravasation apparatus further includes means for comparing the volume of extravasation with a prescribed level of extravasation.

A method for detecting extravasation of a fluid applied to a patient in accordance with the present invention includes the steps of attaching a support pad to a body part of a patient in proximity to a site at which a fluid is to be injected into the patient, radiating, in an encoded manner into the body part at the site at which the fluid is injected into the patient, light from a plurality of light sources mounted to the support pad; and detecting light transmitted from the light sources that is reflected, scattered, diffused or otherwise emitted from the body part individually by a plurality of light detectors mounted to the support pad. This method also includes developing a plurality of light source/light detector pair signals representative of the light detected individually by the light detectors for each of the light sources and developing, prior to injection of the fluid into the body part, a plurality of individual light source/light detector pair baseline signals associated with each light source/ light detector pair and against which measurements made during injection of the fluid into the body part are compared. This method further includes developing from comparisons of the light source/light detector pair signals with the light source/light detector pair baseline signals new light source/light detector pair signals having an improved signal-to-noise ratio. Prior to injection of the fluid into the body part, an extravasation model, dependent on the arrangement of the light sources and the light detectors on said support pad, is developed for calculating extravasation volume from the new light source/light detector pair signals having an improved signal-to-noise ratio. This method further includes combining, according to the extravasation model, the new light source/light detector pair signals having an improved signal-to-noise ratio to determine the volume of extravasation and comparing the determined volume of extravasation with a prescribed level of extravasation.

BRIEF DESCRIPTION OF THE DRAWINGS

The present invention is illustrated by way of examples and not limitation in the accompanying drawings, in which like reference numerals indicate like parts.

FIG. 3A is a schematic diagram of a first embodiment of extravasation detection apparatus constructed in accordance with the present invention.

FIG. 3B is a schematic diagram of a second embodiment of extravasation detection apparatus constructed in accordance with the present invention.

DETAILED DESCRIPTION OF THE INVENTION

The present invention operates by transmitting light, from a plurality of light sources, into the tissue of a patient proximate to an injection site, namely the tissue adjacent to the site of a pharmaceutical infusion. The transmitted light enters the tissue and a portion of the light is reflected, scattered, diffused or otherwise emitted back to the surface of the injection site where it is detected by a plurality of light detectors. The occurrence of extravasation causes the pattern of the detected light to change. Such changes are detected and, when a determination is made that the extravasation exceeds a prescribed level, an alarm can be sounded or the injection unit can be shut off.

The present invention can be utilized at various injection sites, including both percutaneous injections and surgically exposed vasculature injections. For example, the present invention can be used to detect overlying or underlying tissues or in tissues adjacent the needle or catheter tip of an intravascular infusion unit. The present invention is particularly useful in detecting extravasation of imaging agents and the like and can be used with other substances, such as other contrast media, medicinal fluid, electrolytes and pharmaceuticals.

One target application of extravasation detection is monitoring the bolus injections given, for example, in CT scans. In this case, volumes of approximately 150 ml are injected at rates of 1 ml/second to 5 ml/second. A clinically diagnosed extravasation occurs if greater than 5 ml of contrast material leaks during the injection. A monitoring unit, therefore, must discriminate between a true, greater than 5 ml extravasation and (1) a clean in-vein injection of 150 ml, (2) a small less than 4 ml extravasation, and (3) artifacts due to patient movement and the like.

Although the fluids are relatively non-toxic compared with the bolus injections of contrast agents and the infusion rates are slow, after a few hours, an extravasation can induce pooling of sizable volumes resulting in the patient not receiving the prescribed medications or fluid and/or patient discomfort and/or potential morbidity.

The main difference between the bolus injection monitoring applications of extravasation detection and home healthcare IV drip monitoring application, from the unit perspective, is that the timescales are much slower with the IV drip.

Figure 1:
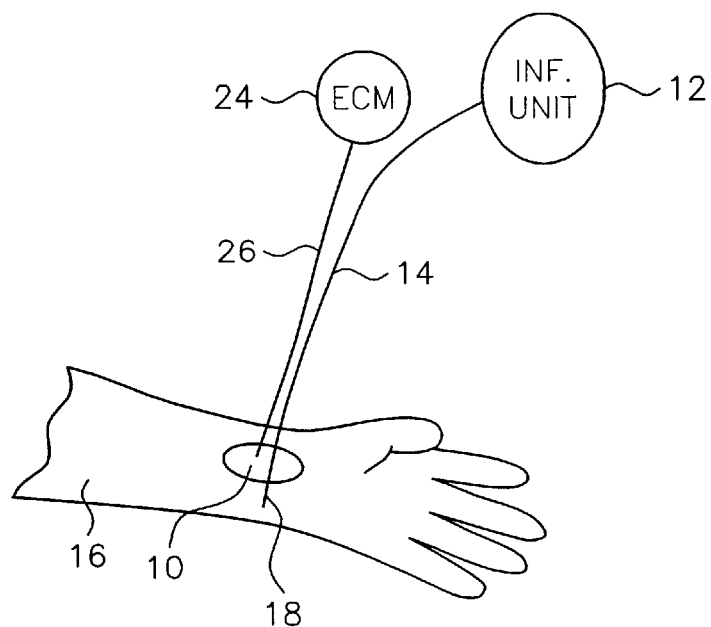
FIG. 1 is a schematic diagram illustrating extravasation detection apparatus, constructed in accordance with the present invention, applied to the wrist of a patient during the infusion of a substance into the wrist of the patient by an infusion unit.

Referring to FIG. 1, extravasation detection apparatus, constructed in accordance with the present invention, includes a support pad 10 adapted for attachment to a body part of a patient in proximity to a site at which a fluid is to be injected into the patient by an infusion unit (INF. UNIT) 12 through a connector tube is 14. For the example illustrated in FIG. 1, fluid is to be injected into the wrist 16 of the patient. The size and shape of support pad 10 depends on the clinical application. For example, support pad 10 is sized and shaped to accommodate an infusion needle 18. The manner of attachment of support pad 10 to the body part also depends on the clinical application. The support pad can be attached to the body part by an adhesive, tape, a wrap-around strap or the like.

Figure 2:
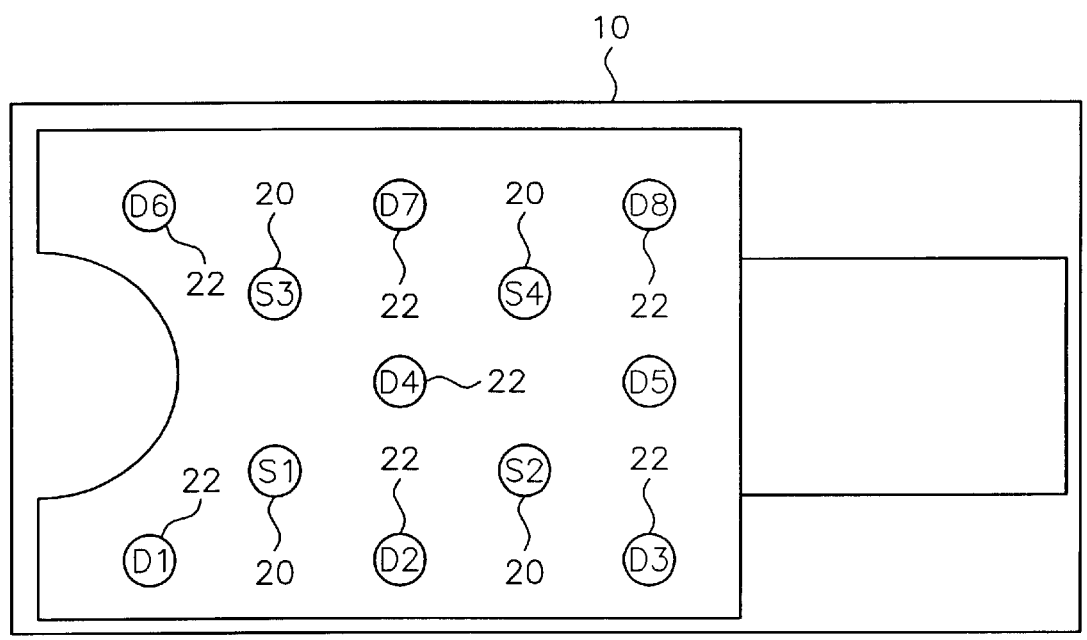
FIG. 2 is a schematic plan view of the support pad portion of extravasation detection apparatus constructed in accordance with the present invention and the pattern of light sources and light detectors mounted to the support.

As shown in FIG. 2, a plurality of light sources 20 is mounted to support pad 10 for radiating light into the body part; for example wrist 16. The particular pattern of light sources 20 will be explained below. Light sources 20 radiate light into a body part of a patient at an infusion site.

Also mounted to support pad 10 is a plurality of light detectors 22 for individually detecting light transmitted from light sources 20 that is reflected, scattered, diffused or otherwise emitted from the body part at an infusion site and for individually developing signals representative of the light detected by the light detectors. The particular pattern of light detectors 22 will be explained below.

Returning to FIG. 1, extravasation detection apparatus, constructed in accordance with the present invention, also includes means for energizing light sources 20 in an encoded manner to radiate light into the body part of a patient in an encoded manner. By encoding each light source energization, each light source energization is given a distinct identification that is useful in processing the signals developed by light detectors 22. Encoding of the light source identifications can be by timing sequence, or by frequency or by phase. The ultimate result of the detection of the light that is reflected, scattered, diffused or otherwise emitted from the body part at an infusion site is the development of a plurality of light source/light detector pair signals representative of the light detected individually by light detectors 22 for each of the light sources 20.

Extravasation detection apparatus, constructed in accordance with the present invention, further includes means responsive to the signals developed by light detectors 22:for determining when extravasation of fluid injected into the body part exceeds a prescribed level. Such means are represented in FIG. 1 by electronics control module (ECM) 24 connected to support pad 10, and more particularly to the light sources 20 and the light detectors 22, by a connector tube 26.

FIGS. 3A through 3D illustrate four preferred embodiments of the present invention. Each of these embodiments includes a support pad 10, an electronic control module 24, and a conduit 26 by which the light sources 20 and the light detectors 22 that are mounted to the support pad are connected to the control module. Conduit 26, having a flexible outer sheath 28 and a connector device 30, and support pad 10 can be arranged as a single unit that is disposable and can be discarded after a single usage and replaced by a new unit.

In the four embodiments of the present invention illustrated by FIGS. 3A through 3D, only one light source 32 and only one light detector 34 is shown in each figure. It will be understood, however, that light is radiated into a patient from a plurality of light sources 20 in accordance with the present invention and that light is received from the patient and detected by a plurality of light detectors 22 in accordance with the present invention as shown by the support pad of FIG. 2 that carries a plurality of light sources and a plurality of light detectors.

In the FIG. 3A embodiment of the present invention, light originates from a light source 32 in electronic control module 24 and light is received and detected by a light detector 34 also in the electronic control module. Light from light source 32 is conducted to support pad 10 for radiation into the patient via an optical source fiber 36 extending through sheath 28 and light received from the patient is conducted from the support pad to light detector 34 via an optical detector fiber 38 also extending through sheath 28. It will be understood that the number of optical source fibers 36 needed is dependent upon the number of light sources 32 in electronic control module 24 and the number of optical detector fibers 38 needed is dependent upon the number of light detectors in electronic control module 24. In this embodiment of the invention, the tips 36a of optical source fibers 36 serve as the plurality of light sources mounted to support pad 10 for radiating light into the body part of the patient and the tips 38a of optical detector fibers 38 serve as the plurality of light detectors mounted to support pad 10 for individually detecting light transmitted from the light sources that is reflected, scattered, diffused or otherwise emitted from the body part of the patient. The arrangement illustrated in FIG. 3A allows light sources 32, in electronic control module 24, and light detectors 34, also in electronic control module 24, to be retained when a unit composed of support pad 10 and conduit 26 is discarded.

In the FIG. 3B embodiment of the present invention, light originates from a light source 40 mounted to support pad 10, while light detector 42 is in electronic control module 24. A conductor 44, extending through sheath 28, conducts a signal from electronic control module 24 to energize light source 40. As with the embodiment of FIG. 3A, light received from the patient is conducted from the support pad 10 to light detector 34 via an optical detector fiber 38 also extending through sheath 28. In this embodiment of the invention, the tips 38a of optical detector fibers 38 serve as the plurality of light detectors mounted to support pad 10 for individually detecting light transmitted from the light sources that is reflected, scattered, diffused or otherwise emitted from the body part of the patient.

Figure 3C:
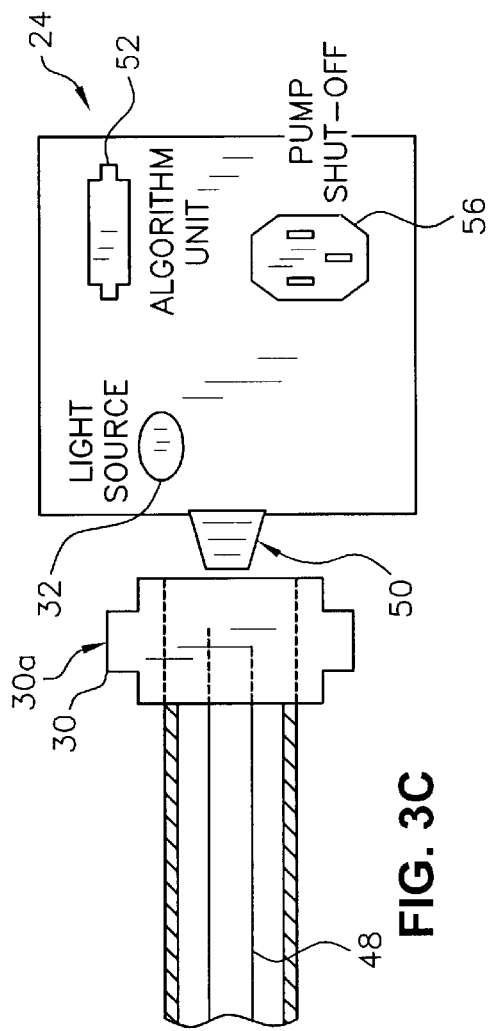
FIG. 3C is a schematic diagram of a third embodiment of extravasation detection apparatus constructed in accordance with the present invention.

In the FIG. 3C embodiment of the present invention, a light detector 46 is mounted to support pad 10, while light source 32 is in electronic control module 24. A conductor 48, extending through sheath 28, conducts a signal developed by light detector 46 to electronic control module 24. As with the embodiment of FIG. 3A, light originates from a light source 32 in electronic control module 24 and is conducted to support pad 10 via an optical source fiber 36 also extending through sheath 28. In this embodiment of the invention, the tips 36a of optical source fibers 36 serve as the plurality of light sources mounted to support pad 10 for radiating light into the body part of the patient.

Figure 3D:
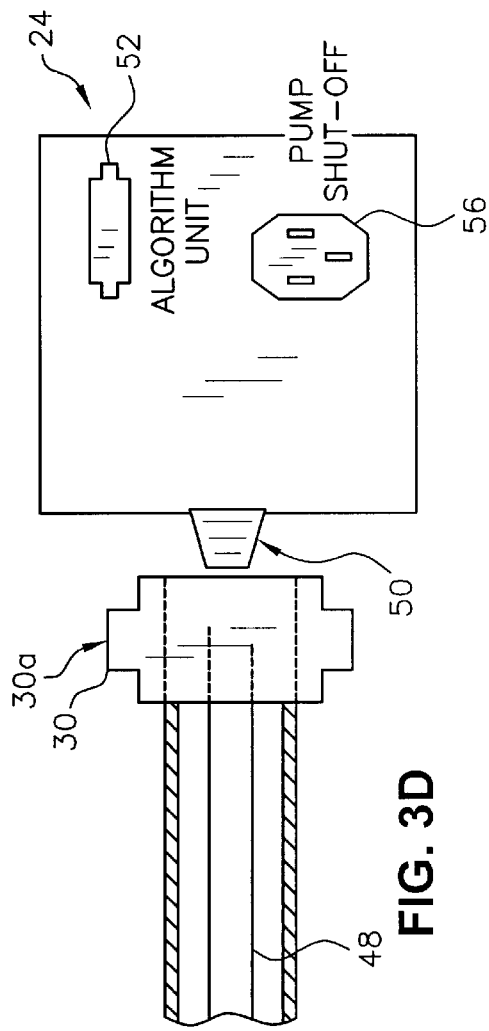
FIG. 3D is a schematic diagram of a fourth embodiment of extravasation detection apparatus constructed in accordance with the present invention.
Figure 4:
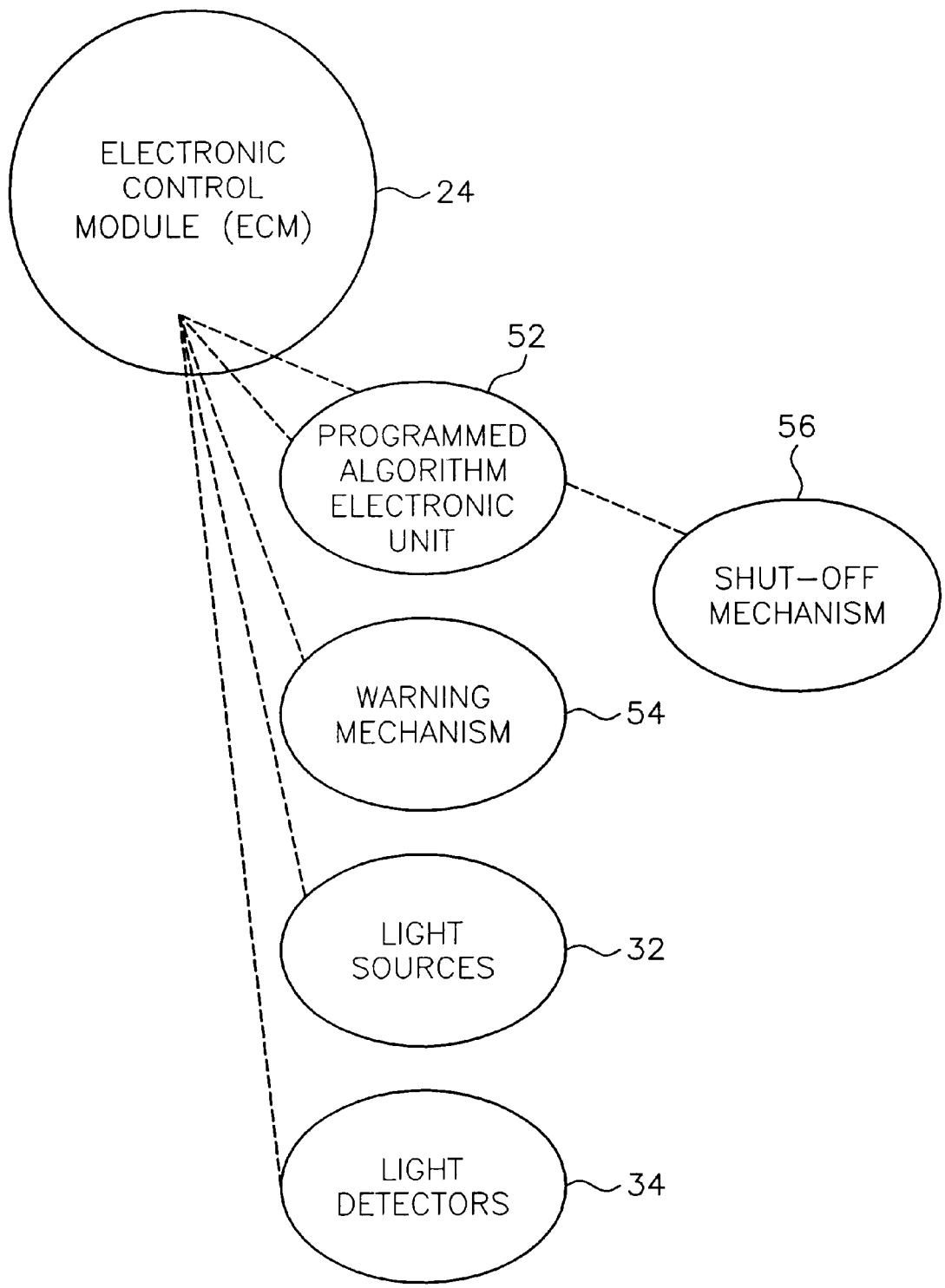
FIG. 4 is a block diagram of the electronic control module portion of extravasation detection apparatus constructed in accordance with the present invention.

In the FIG. 3D embodiment of the present invention, a light source 40 is mounted to support pad 10 and a light detector 46 also is mounted to support pad 10. A conductor 44, extending through sheath 28, conducts a signal from electronic control module 24 to energize light source 40 and conductor 48, also extending through sheath 28, conducts a signal developed by light detector 46 to electronic control module 24.

In the preferred construction, connector device 30 includes an outer hub 30a surrounding the end of sheath 28 and designed to interlock with port 50 of electronic control module 24. Connector device 30 aligns the optical fibers and wires extending through sheath 28 with associated parts in the electronic control module for optical and electrical communication between associated parts. The particular mechanism by which connector device 30 interlocks with port 50 can be a luer fitting or a threaded connection or a snap-fit or another form of co-axial connection.

Electronic control module 24 includes means to: (a) interpret optically-generated signals, namely the signals developed by the light sensors mounted to support pad 10 or in the electronic control module, (b) process these signals, and (c) provide a warning signal and/or a pump shut-off signal and/or a signal for coupling a neutralizing agent to reduce potential harm to the patient when extravasation occurs. To perform these tasks, electronic control module 24 can include one or more computers or microprocessors. Electronic control module 24 is preferably, but not necessarily, programmable by an operator. For example, electronic control module 24 can be programmed via a keyboard incorporated in the electronic control module. In addition, electronic control module 10 can have an input for an auxiliary pre-programmed device such as an electronic strip.

Referring to FIGS. 3A through 3D and 4, electronic control module 24 preferably includes: (a) a programmed algorithm electronic unit 52 that interprets the information in the signals representative of the light received by light detectors 22 of FIG. 2, light detectors 34 of FIGS. 3A and 3B, and light detectors 46 of FIGS. 3C and 3D and outputs warning and/or shut-off signals when the input signals indicate that extravasation has occurred; (b) an audible and/or visible warning mechanism 54, and (c) a shut-off mechanism 56. If arranged according to the FIGS. 3A and 3C embodiments of the present invention, electronic control module 24 also includes the light sources and, if arranged according to the FIGS. 3A and 3B embodiments of the present invention, electronic control module 24 also includes the light detectors. Although considered above as a single unit, the various parts of the electronic control module can be separately packaged.

Figure 5A:
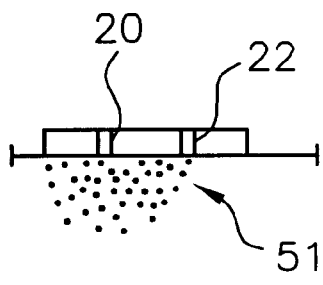
FIG. 5A is a schematic diagram the support pad portion of extravasation detection apparatus constructed in accordance with the present invention applied to a body part.
Figure 5B:
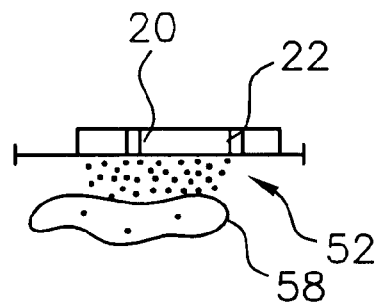
FIG. 5B is a schematic diagram the support pad portion of extravasation detection apparatus constructed in accordance with the present invention applied to a body part during extravasation.

As shown by FIGS. 5A, with no extravasation of the infused substance, light that is radiated into a patient from a light source 20 can have a photon migration pattern of S1. When there is extravasation of the infused substance, as represented by reference numeral 58 in FIG. 5B, the photon migration pattern is changed to another pattern S2 because of scattering or absorption changes. This change in the photon migration pattern can result in variations of the detected light received by a light detector 22, such that extravasation can be detected. As indicated above, it is contemplated that the number of light sources and the number of light detectors can be varied and the distribution and spacing of the light sources and light detectors can also be varied depending on the particular situation or conditions at hand. It is also contemplated that the light transmission can include, for example, continuous wave transmission, intermittent transmission, and modulated frequency transmission. In addition, it is contemplated that the light detection can include, for example, scattering, absorption, and fluorescence.

Figure 6:
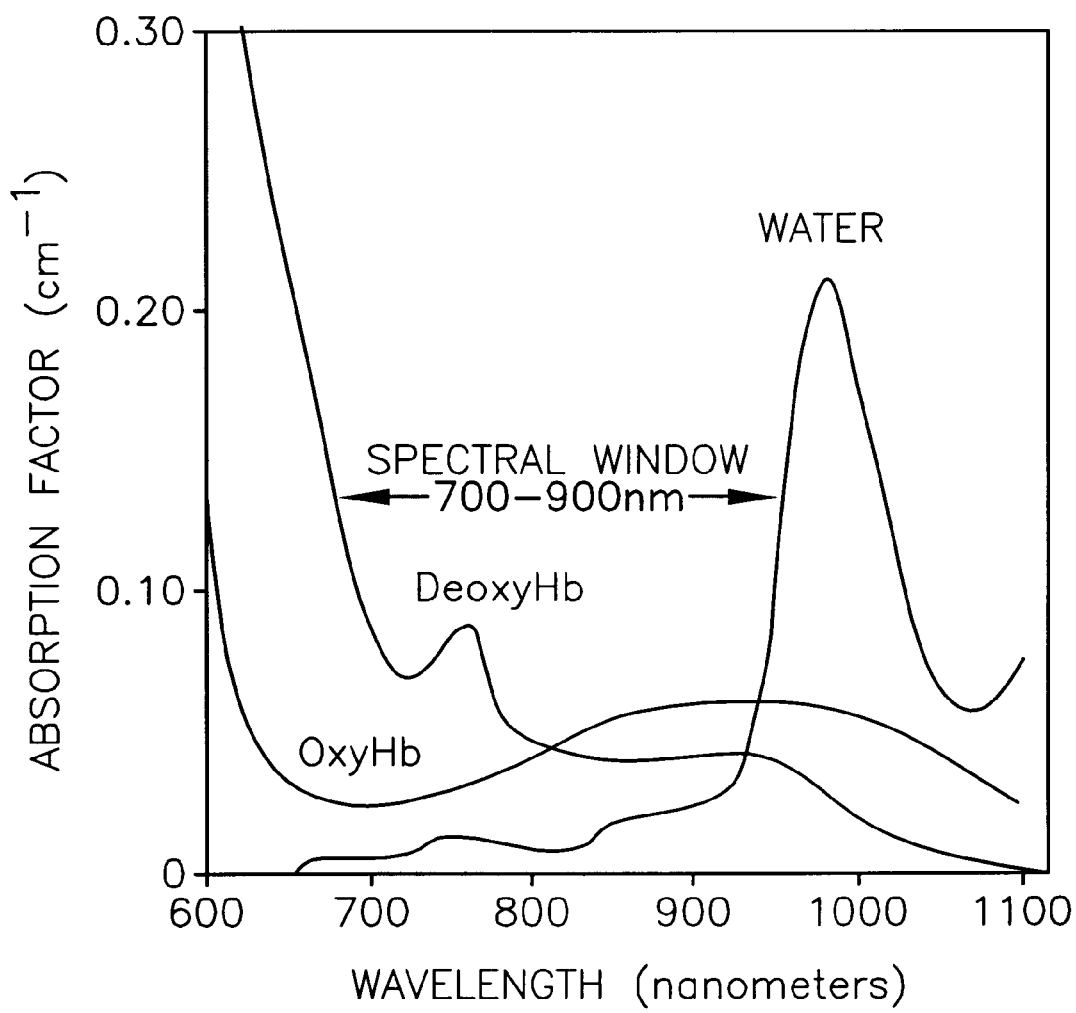
FIG. 6 is a graph of light absorption versus the wavelength of light radiated into the patient that shows the preferred wavelength to facilitate extravasation detection.

The light radiated into the patient is preferably within a particular spectral range, or spectral window, as illustrated in the graph of FIG. 6. Most preferably, the wavelength of light radiated is between 700 and 900 nanometers. In this manner, the absorption factors of water, oxyhemoglobin and deoxyhemoglobin are minimized to facilitate extravasation detection.

Figure 7:
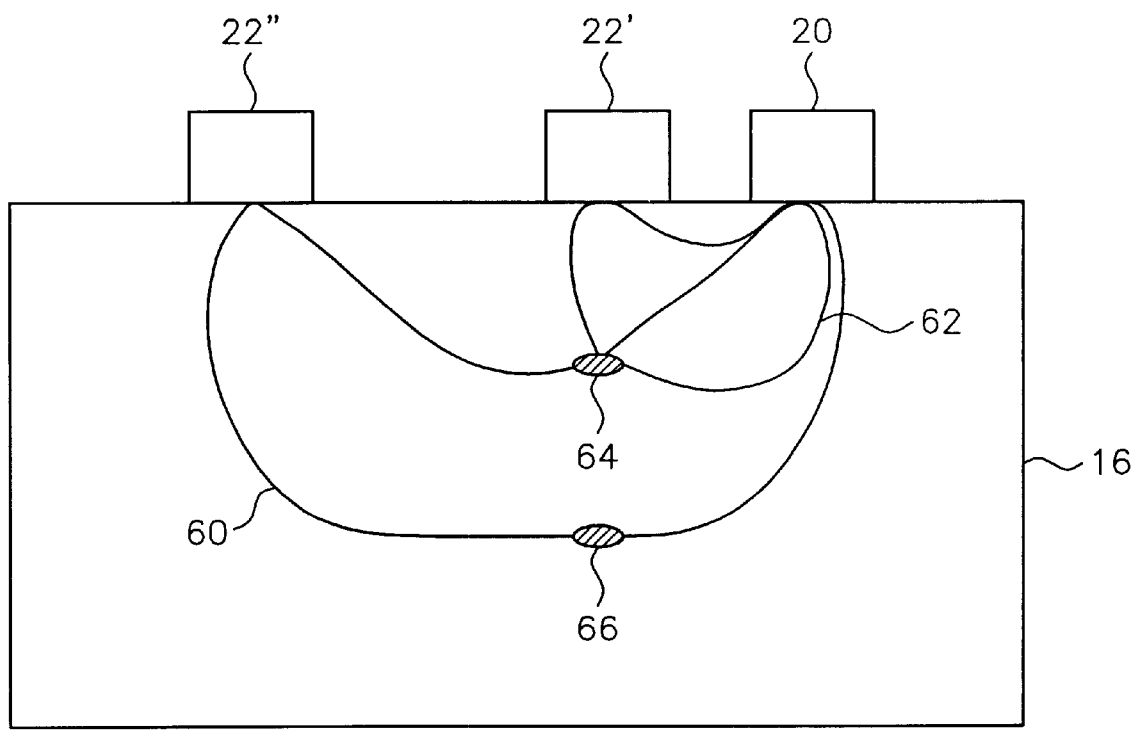
FIG. 7 illustrates schematically the manner in which light source/light detector pairs of FIG. 2 function to develop signals from which extravasation can be determined.

FIG. 7 illustrates schematically the manner in which light source/light detector pairs function to develop signals from which extravasation can be determined. Light source 20 radiates light into body part 16 (e.g. the wrist) at an infusion site. Light from light source 20 is detected by light detectors 22' and 22" as indicated by sensitivity contours 60 and 62, respectively. The sensitivity is higher inside the contours and lower outside the contours. The location and size of objects 64 and 66 (e.g. extravasation of an infused fluid) will affect the transmission of light from light source 20 to light detectors 22' and 22" and in different ways.

Objects 64 and 66 (e.g., extravasations) will induce the same signal in light detector 22" for light source 20/light detector 22" pair because both objects are located on the same sensitivity contour, namely sensitivity contour 60. In contrast, light detector 22' will record a much larger signal for light source 20/light detector 22' pair for object 64 than will light source 22' for light source 20/light detector 22' pair for object 66 because object 64 is in a higher sensitivity region, namely on or in close proximity to sensitivity contour 62, while object 66 is spaced from sensitivity contour 62. In general, both the size and the location of an object affect the light transmitted from a light source through the body part to a light detector. It should be noted that the same size objects can result in significantly different signals developed by a light detector because the distances of the objects from the sensitivity contour associated with the light source/light detector pair are significantly different. Generally, the greater the depths of the object in the body part, the smaller the signals developed by the light detectors. Objects located the same distance from the sensitivity contour associated with the light source/light detector pair can result in significantly different signals developed by the light detector because the sizes of the objects are significantly different. The greater the size of the object in the body part, the larger the signals developed by the light source/light detector pairs. By combining the information from light source/light detector pairs with different separations and different locations, the volume of the extravasation object can be determined independent of the depth and the location of the object.

The described process of combining a group of spatially distinct surface measurements to characterize the internal properties of a prescribed tissue volume falls under the general topic of diffuse optical tomography. The apparatus and method of the present invention use encoded multiple light source/light detector pair measurements and modified tomographic algorithms to distinguish between the size of the object and the proximity of the object to the sensitivity contours, so that the degree of extravasation can be determined.

An arrangement of light sources and light detectors, such as light sources 20 and light detectors 22 illustrated in FIG. 2, monitor the light transmission through the body tissue at an infusion site. Whenever light, transmitted from a light source, is detected by a light detector, a light source/light detector pair is established. The raw measurements of light transmission are recorded as voltages received from the light detectors. For each light source/light detector 20/22 pair, a voltage $V_i$ is recorded. For example, for three light sources and three light detectors which detect light from all three light sources, the voltages developed by the light detectors are:

|  | Light Detector 1 | Light Detector 2 | Light Detector 3 |
| --- | --- | --- | --- |
| Light Source 1 | V11 | V12 | V13 |
| Light Source 2 | V21 | V22 | V23 |
| Light Source 3 | V31 | V32 | V33 |

For a description of a single light source/light detector pair electronics channel, see Siegel A. M., Marota, J. J. A., Boas D. A., "Design and evaluation of a continuous-wave diffuse optical tomography system" *OPTICAL EXPRESS*, 4: (8) 287–298 Apr. 12 1999.

An algorithm then is used to combine the voltages into a single effective measurement of the extravasation volume. Generally this can be stated as:

$$V_{ext}(t) = \sum_{i}^{N} F_i(t) \otimes V_i(t) \tag{1}$$

where:
$V_{ext}$ is the time variant measure of the extravasated volume,
$v_i(t)$ are the time variant voltages for each light source/light detector pair, and
$F_i(t)$ is a time variant functional operator acting on $v_i(t)$ as defined in the signal processing described below.
It should be noted that $F_i(t)$ may depend on some combination of $v_j(t_2)$ where j is any light source/light detector pair index and $t_2$ is any time <t.

The following algorithms are methods of combining the light transmission voltages into a single effective measurement of the extravasation volume. The algorithms are developed as follows.

A model for calculating extravasation volume is developed prior to injection of a fluid into the patient. This model is dependent, at least, upon the arrangement of light sources 20 and light detectors 22 on support pad 10 and, preferably, also dependent upon the tissue optical properties of the body part into which the fluid is injected, such as absorption and scattering. In vivo measurements of known extravasation volumes are made on sources other than the patient and used to determine the parameters of the model.

Figure 8:
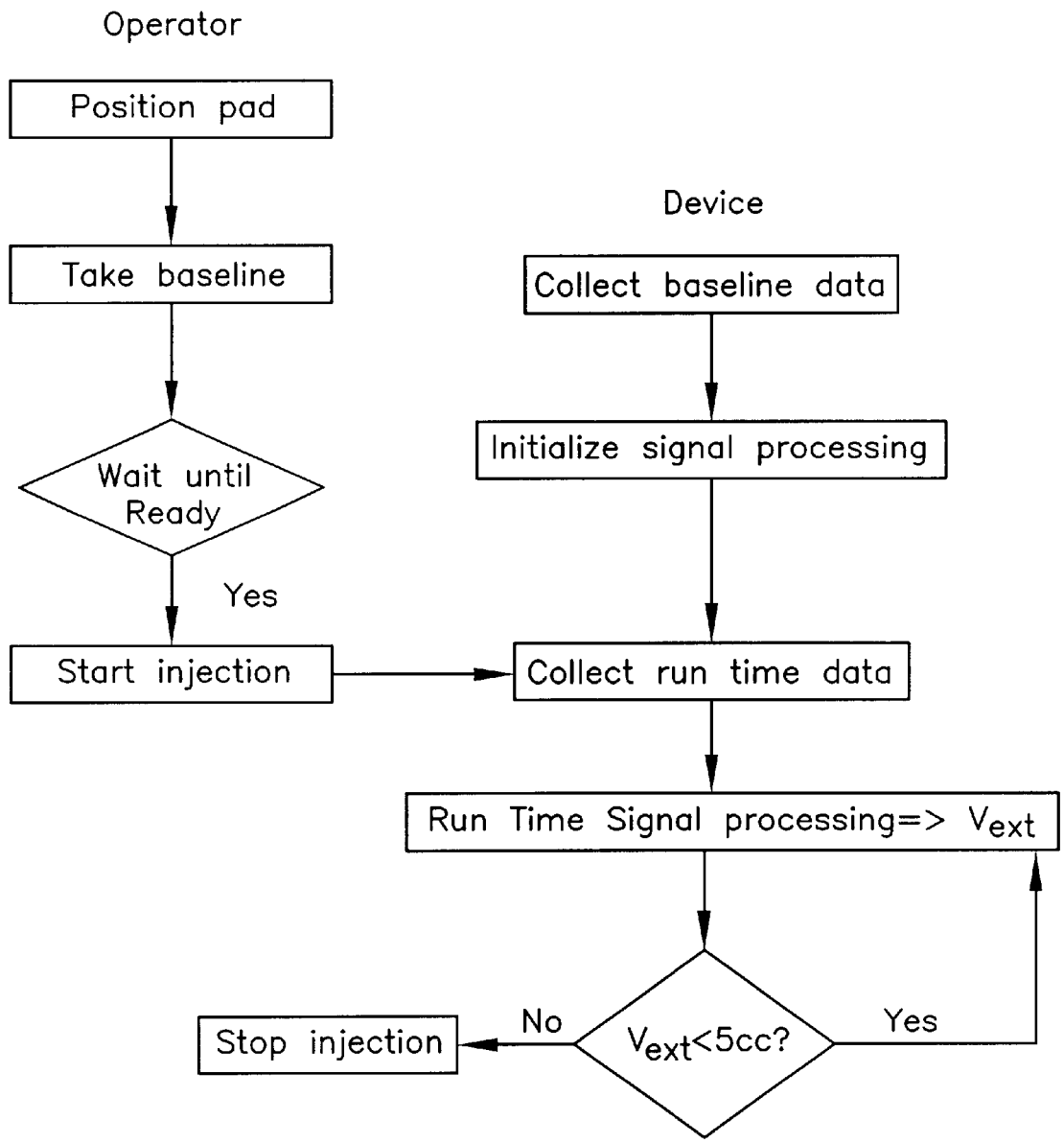
FIG. 8 is a flow chart of the algorithm by which the signals to the light sources of FIG. 2 and signals developed by the light detectors of FIG. 2 are processed.

Each algorithm has a group of signal processing procedures that can be used separately or in combination with others. The general detection scheme is depicted in FIG. 8 which is a flow chart of the algorithm by which the signals to the light sources of FIG. 2 and signals developed by the light detectors of FIG. 2 are processed. It should be noted that during operation, signal processing occurs in two phases, namely an initialization phase and a run time phase.

(A) Developing New Light Source/Light Detector Pair Signals Having Improved Signal-to-Noise Ratio Prior to injection of the fluid into the body part, a plurality of individual light source/light detector pair baseline signals, associated with each of the light detectors 22, are developed. The light source/light detector pair signals developed by detectors 22 during injection of the fluid into the body part are compared against the baseline signals and new light source/light detector pair signals having an improved signal-to-noise ratio are developed from these comparisons.

Each voltage measured for each light source 20/light detector 22 pair ($v_i$) first is converted into a baseline differential light source/light detector pair signal $D_i$ according to the following equation:

$$D_i(t) = \ln\left(\frac{v_i(t)}{v_{i0}}\right) \quad (2)$$

where:

$v_i(t)$ is the instantaneous voltage, and $<v_{i0}>$ is the average voltage during the baseline time interval Optionally, the signal can be defined as a difference signal where $D_i(t) = v_i(t) - <v_{i0}>$. The method defined by equation (2) is preferred.

It is understood that the baseline signal is defined conceptually to be calculated from a weighted average of the signal before time t. In practice, the baseline signal can be continually recalculated to provide a running baseline value.

Next, the baseline differential light source/light detector pair signals are processed into the new light source/light detector pair signals having an improved signal-to-noise ratio by one or more of the following:

(1) multiplying each baseline differential light source/light detector pair signal $D_i$ by the signal-to-noise ratio in the associated light source/light detector pair baseline signal:

$$S_i(t) = \frac{v_{i0}}{N_{i0}} D_1(t) \quad (3)$$

where $N_{i0}$ is the noise in $v_{i0}$.

(2) removing signal components from each baseline differential light source/light detector pair signal $D_i$ that correlate with other light source/light detector pair signals, as is described in detail in "Optimum Signal Processing, An Introduction", S. J. Orfanidis, McGraw-Hill, 1988, section "correlation canceling" page 9–15, and (3) removing signal components from each baseline differential light source/light detector pair signal $D_i$ that correlate with physiologic functions of the patient.

Other noise weighting techniques, as described in "Optimum Signal Processing, An Introduction", S. J. Orfanidis, McGraw-Hill, 1988, are incorporated herein by reference.

(B) Developing Extravasation Model

As indicated above, prior to injection of the fluid into the body part, an extravasation model, dependent on the arrangement of the light sources 20 and the light detectors 22 on the support pad 10, is developed. This model is used for calculating extravasation volume from the new light source/light detector pair signals having an improved signal-to-noise ratio. Developing the extravasation model includes:

(a) developing, prior to injection of the fluid into the body part, signals similar to the new light source/light detector pair signals having an improved signal-to-noise ratio from sources other than the patient, (b) calculating a parameter-dependent extravasation volume from the signals similar to the new light source/light detector pair signals having an improved signal-to-noise ratio, and (c) determining the parameters of the parameter-dependent extravasation volume by making, prior to injection of the fluid into the body part, in vivo measurements of known extravasation volumes in the sources other than the patient.

The step of calculating a parameter-dependent extravasation volume V(t) can be carried out in one of three ways. All three ways can be expressed by the following equation:

$$V(t) = \frac{\alpha}{N} \sum_i^N C_i S_i(t) \quad (4)$$

where:

$C_i$ is a weighting coefficient for each new light source/light detector pair signal having an improved signal-to-noise ratio $\alpha$ is a correction factor corresponding to an empirically determined parameter to correct for model inaccuracies, and N is the number of source detector pairs.

The first way of carrying out the calculation of the parameter-dependent extravasation volume involves:

(a) developing a sum signal that is the sum of the magnitudes of the new light source/light detector pair signals having an improved signal-to-noise ratio which is equivalent to assuming that all the coefficients $C_i$ of equation (4) are equal, namely $C_i=1$, and (b) multiplying the sum signal by $\alpha$, a correction factor corresponding to an empirically determined parameter to correct for model inaccuracies.

The second way of carrying out the calculation of the parameter-dependent extravasation volume involves:

(a) selecting separate coefficients for:

(1) positive values of the new light source/light detector pair signals having an improved signal-to-noise ratio, (i.e. for $S_i(t)>0$, $C_i=\beta$ and (2) negative values of the new light source/light detector pair signals having an improved signal-to-noise ratio (i.e. for $S_i(t)<0$, $C_i=\gamma$ (b) multiplying:
  (1) positive new light source/light detector pair signals having an improved signal-to-noise ratio by the positive value coefficients, and
  (2) negative new light source/light detector pair signals having an improved signal-to-noise ratio by the negative value coefficients,
(c) developing a sum signal of the new light source/light detector pair signals having an improved signal-to-noise ratio multiplied by the positive value coefficients and the new light source/light detector pair signals having an improved signal-to-noise ratio multiplied by the negative value coefficients, and
(d) multiplying the sum signal by a correction factor corresponding to an empirically determined parameter to correct for model inaccuracies.

The third way of carrying out the calculation of the parameter-dependent extravasation volume involves:
(a) combining the new light source/light detector pair signals having an improved signal-to-noise ratio into a differential absorption image representative of the change in the spatially variant absorption from baseline,
(b) combining the new light source/light detector pair signals having an improved signal-to-noise ratio into a differential scattering image representative of the change in the spatially variant scattering from baseline,
(c) developing a sum absorption signal by performing a volume sum of the differential absorption image,
(d) developing a sum scattering signal by performing a volume sum of the differential scattering image,
(e) multiplying the sum absorption signal by a correction factor corresponding to an empirically determined parameter to correct for model inaccuracies,
(f) multiplying the sum scattering signal by a correction factor corresponding to an empirically determined parameter to correct for model inaccuracies, and
(g) adding the result of multiplying the sum absorption signal by a correction factor corresponding to an empirically determined parameter to correct for model inaccuracies and the result of multiplying the sum scattering signal by a correction factor corresponding to an empirically determined parameter to correct for model inaccuracies.

With respect to steps (a) and (b) described above, wherein differential images are obtained, the dominant optical signal contrast due to extravasation results from the contrast in the scattering coefficient. There is also a contrast due to absorption. Here, a procedure is described for analyzing the scattering contrast, although absorption contrast will follow the same procedure with the necessary adjustments to the weight matrix. See O'Leary, M. A., Boas, D. A., Chance, B., Yodh, A. G., "Experimental Images of Heterogeneous Turbid Media By Frequency-Domain Diffusing Photon Tomography" OPTICS LETTERS, 20: (5) 426–428 Mar. 1, 1995.

Consider a monitored volume that is binned into M voxels (j). An expression for the extravasation volume can be written as a sum of the local voxel scattering changes:

$$V_{ext} = \alpha \sum_j^M \delta\mu_s^{\prime j} \tag{5}$$

Therefore, by quantifying the volume integrated changes in the scattering coefficient, a measure of the extravasation volume is provided. An image reconstruction scheme maps the measurements $S_i$ onto the voxels through a matrix W. Mathematically this can be expressed as:

$$\delta\mu_{sj}' = \sum_i^N \tilde{W}_{ij} S_i \tag{6}$$

Substituting this for expression musp into the expression for $V_{ext}$ leads to:

$$V_{ext} = \alpha \sum_i^N \sum_j^M \tilde{W}_{ij} S_i \tag{7}$$

and finally:

$$C_i = N \sum_j^M \tilde{W}_{ij} \tag{8}$$

As discussed by O'Leary et al., cited above, and others, the matrix $\tilde{W}_{ij}$ can be obtained by inverting the rytov weight matrix defined by $$W_{ij} = \frac{\nabla G(r_{si}, r_j) \nabla G(r_j, r_{di}) vh^3}{G(r_{si}, r_{di})} \tag{9}$$

where:
  G is the semi-infinite greens function $$G(r, r') = G_0 \left( \frac{e^{-k|r-r'|}}{|r-r'|} \right) \tag{10}$$

with attenuation coefficient $k=\sqrt{3\mu_a\mu_s'}$, and normalization constant $G_0$, and
$vh^3$ is the voxel element of the bining.

Because a signal-to-noise weighted expression has been used for the scattered wave, the weights are modified such that $$W_{ij}^{ours} = \frac{\langle v_{iO} \rangle}{N_{iO}} w_{ij}^{rytov} \tag{11}$$

In general, many problems can arise when inverting W. See.Arridge, S. R., "Optical tomography in medical imaging" Inverse Problems, 15 (1999) R41–R93. Noise can be greatly amplified and the process yields images of little use. To control the noise, regularization procedures are used. See Arridge and O'Leary et al. cited above. These regularization procedures reduce the image resolution obtainable. However, in this particular application, images are not of interest; only an integrated volumetric measurement of an injected fluid is of interest. Therefore, very stable, low resolution parameters are used.

In addition, the computation time can be prohibitive (e.g. minutes to days). See Arridge and O'Leary et al. cited above. But again, in this use, the weights are summed over the entire monitoring volume that reduces the coefficients to the number of detectors used.

Two of the main complications involved with image reconstructions are avoided, namely noise instabilities and speed, by performing a volume sum. During the baseline phase, the optical properties ($\mu_{eff}$) are obtained and the weight matrix is computed, inverted and volume summed to give the sensitivity coefficients $C_i$. During runtime, the coefficients are fixed.

In summary and referring to FIG. 8, an operator positions support pad 10 on the body part of the patient. Collection of baseline data can be initiated either by the operator or automatically by the apparatus when support pad 10 is positioned on the patient. When the functionings of the initialization stage have been completed and the signal levels meet a stability criteria, the apparatus signals that it is ready to monitor an injection. At that point, the operator can start the injection. While the injection is occurring, the apparatus continually calculates an extravasation volume. If the extravasation volume exceeds the prescribed threshold, the injection is stopped.

It is understood that extravasation detection apparatus, constructed in accordance with the present invention, can have multiple light sources and multiple light detectors as described and illustrated, or a single light source and multiple light detectors, or multiple light sources and a single light detector. The underlying signal processing concept, described above in connection with multiple light sources and multiple light detectors, can be employed with to the two alternatives. When, for example, only a single light source is employed, encoding the light source is trivial in that there is only one source of light. It will be understood that energizing a single light source, nonetheless, is considered energizing the light source in an encoded manner.

While the present invention has been illustrated and described with reference to preferred embodiments presently contemplated as best modes for carrying out the invention, it is understood that various changes may be made in adapting the invention to different embodiments without departing from the broader inventive concepts disclosed herein and comprehended by the claims which follow.

What is claimed:

1. Extravasation detection apparatus comprising:
    a support pad adapted for attachment to a body part of a patient in proximity to a site at which a fluid is to be injected into the patient;
    a plurality of light sources, mounted to said support pad, for radiating light into the body part;
    means for energizing said light sources in an encoded manner to radiate light into the body part in an encoded manner;
    a plurality of light detectors, mounted to said support pad, for:
        (a) individually detecting light transmitted from said light sources that is reflected, scattered, diffused or otherwise emitted from the body part, and
        (b) individually developing light source/light detector pair signals representative of the light detected individually by said light detectors;
    means for developing, prior to injection of the fluid into the body part, a plurality of individual light source/light detector pair baseline signals associated with each light source/light detector pair and against which measurements made during injection of the fluid into the body part are compared;
    means for comparing the light source/light detector pair signals with the associated light source/light detector pair baseline signals;
    means for developing from the comparisons of the light source/light detector pair signals with the associated light source/light detector pair baseline signals new light source/light detector pair signals having an improved signal-to-noise ratio;
    means for developing, prior to injection of the fluid into the body part, a model, dependent on the arrangement of said light sources and said light detectors on said support pad, for calculating extravasation volume from the new light source/light detector pair signals having an improved signal-to-noise ratio;
    means for combining, according to the extravasation model, the new light source/light detector signals having an improved signal-to-noise ratio to determine the volume of extravasation; and
    means for comparing the volume of extravasation with a prescribed level of extravasation.

2. Extravasation detection apparatus according to claim 1 wherein the extravasation model also is dependent upon tissue optical properties of the body part into which the fluid is injected.

3. Extravasation detection apparatus according to claim 2 wherein the means for developing the extravasation model include:
    (a) means for developing, prior to injection of the fluid into the body part, signals similar to the new light source/light detector pair signals having an improved signal-to-noise ratio from sources other than the patient,
    (b) means for calculating a parameter-dependent extravasation volume from the signals similar to the new light source/light detector pair signals having an improved signal-to-noise ratio, and
    (c) means for determining the parameters of the parameter-dependent extravasation volume by making, prior to injection of the fluid into the body part, in vivo measurements of known extravasation volumes in the sources other than the patient.

4. Extravasation detection apparatus according to claim 3 wherein the means for calculating a parameter-dependent extravasation volume from the signals similar to the new light source/light detector pair signals having an improved signal-to-noise ratio include:
    (a) means for developing a sum signal that is the sum of the magnitudes of the new light source/light detector pair signals having an improved signal-to-noise ratio, and
    (b) means for multiplying the sum signal by a correction factor corresponding to an empirically determined parameter to correct for model inaccuracies.

5. Extravasation detection apparatus according to claim 3 wherein the means for calculating a parameter-dependent extravasation volume from the signals similar to the new light source/light detector pair signals having an improved signal-to-noise ratio include:
    (a) means for selecting separate coefficients for:
        (1) positive values of the new light source/light detector pair signals having an improved signal-to-noise ratio, and
        (2) negative values of the new light source/light detector pair signals having an improved signal-to-noise ratio,
    (b) means for multiplying:
        (1) positive new light source/light detector pair signals having an improved signal-to-noise ratio by the positive value coefficients, and
        (2) negative new light source/light detector pair signals having an improved signal-to-noise ratio by the negative value coefficients,
    (c) means developing a sum signal of the new light source/light detector pair signals having an improved signal-to-noise ratio multiplied by the positive value coefficients and the new light source/light detector pair signals having an improved signal-to-noise ratio multiplied by the negative value coefficients, and (d) means for multiplying the sum signal by a correction factor corresponding to an empirically determined parameter to correct for model inaccuracies.

6. Extravasation detection apparatus according to claim 3 wherein the tissue optical properties of the body part include absorption and scattering and the means for calculating a parameter-dependent extravasation volume from the signals similar to the new light source/light detector pair signals having an improved signal-to-noise ratio include:

(a) means for combining the new light source/light detector pair signals having an improved signal-to-noise ratio into a differential absorption image representative of the change in the spatially variant absorption from baseline, (b) means for combining the new light source/light detector pair signals having an improved signal-to-noise ratio into a differential scattering image representative of the change in the spatially variant scattering from baseline, (c) means for developing a sum absorption signal by performing a volume sum of the differential absorption image, (d) means for developing a sum scattering signal by performing a volume sum of the differential scattering image, (e) means for multiplying the sum absorption signal by a first correction factor corresponding to an empirically determined parameter to correct for model inaccuracies, (f) means for multiplying the sum scattering signal by a correction factor corresponding to an empirically determined parameter to correct for model inaccuracies, and (g) means for adding the result of multiplying the sum absorption signal by a first correction factor corresponding to an empirically determined parameter to correct for model inaccuracies and the result of multiplying the sum scattering signal by a second correction factor corresponding to an empirically determined parameter to correct for model inaccuracies.

7. Extravasation detection apparatus comprising:

a support pad adapted for attachment to a body part of a patient in proximity to a site at which a fluid is to be injected into the patient;

a plurality of light sources, mounted to said support pad, for radiating light into the body part;

means for energizing said light sources in an encoded manner to radiate light into the body part in an encoded manner;

a plurality of light detectors, mounted to said support pad, for:

(a) individually detecting light transmitted from said light sources that is reflected, scattered, diffused, or otherwise emitted from the body part, and (b) individually developing light source/light detector pair signals representative of the light detected individually by said light detectors;

means for supplying a plurality of individual light source/light detector pair baseline signals associated with each said light source/light detector pairs and developed prior to injection of the fluid into the body part;

means for comparing the light source/light detector pair signals with the associated light source/light detector pair baseline signals;

means for developing, from the comparisons of the light source/light detector pair signals with the associated light source/light detector pair baseline signals, new light source/light detector pair signals having an improved signal-to-noise ratio;

means for supplying a model, dependent on the arrangement of said light sources and said light detectors on said support pad and developed prior to injection of the fluid into the body part for calculating extravasation volume;

means for combining, according to the extravasation model, the new light source/light detector pair signals having an improved signal-to-noise ratio to determine the volume of extravasation; and means for comparing the determined volume of extravasation with a prescribed level of extravasation.

8. Extravasation detection apparatus according to claim 7 wherein the extravasation model also is dependent upon tissue optical properties of the body part into which the fluid is injected.

9. A method for detecting extravasation of a fluid applied to a patient comprising the steps of:

attaching a support pad to a body part of a patient in proximity to a site which a fluid is to be injected into the patient;

radiating, in an encoded manner into the body part at the site at which he fluid is injected into the patient, light from a plurality of light sources mounted to aid support pad;

detecting light transmitted from said light sources that is reflected, scattered, diffused or otherwise emitted from the body part individually by a plurality of light detectors mounted to said support pad;

developing a plurality of light source/light detector pair signals representative of the light detected individually by said light detectors for each of said light sources;

developing, prior to injection of the fluid into the body part, a plurality of individual light source/light detector pair baseline signals associated with each said light source/light detector pairs and against which measurements made during injection of the fluid into the body part are compared;

developing from comparisons of the light source/light detector pair signals with the light source/light detector pair baseline signals new light source/light detector pair signals having an improved signal-to-noise ratio;

developing, prior to injection of the fluid into the body part, an extravasation model, dependent on the arrangement of said light sources and said light detectors on said support pad, for calculating extravasation volume from the new light source/light detector pair signals having an improved signal-to-noise ratio;

combining, according to the extravasation model, the new light source/light detector pair signals having an improved signal-to-noise ratio to determine the volume of extravasation; and comparing the determined volume of extravasation with a prescribed level of extravasation.

10. A method for detecting extravasation of a fluid applied to a patient according to claim 9 wherein the extravasation model also is dependent upon tissue optical properties of the body part into which the fluid is injected.

11. A method for detecting extravasation of a fluid applied to a patient according to claim 10 wherein the step of developing the extravasation model includes:

(a) developing, prior to injection of the fluid into the body part, signals similar to the new light source/light detector pair signals having an improved signal-to-noise ratio from sources other than the patient, (b) calculating a parameter-dependent extravasation volume from the signals similar to the new light source/light detector pair signals having an improved signal-to-noise ratio, and (c) determining the parameters of the parameter-dependent extravasation volume by making, prior to injection of the fluid into the body part, in vivo measurements of known extravasation volumes in the sources other than the patient.

12. A method for detecting extravasation of a fluid applied to a patient according to claim 11 wherein the step of developing the new light source/light detector pair signals having an improved signal-to-noise ratio includes:

(a) developing baseline differential light source/light detector pair signals by one of:
  (1) the difference between each light source/light detector pair signal and the associated light source/light detector pair baseline signal, and
  (2) the log of each light source/light detector pair signal divided by the associated light source/light detector pair baseline signal, and (b) processing the baseline differential light source/light detector pair signals into the new light source/light detector pair signals having an improved signal-to-noise ratio by at least one of:
  (1) multiplying each baseline differential light source/light detector pair signal by the signal-to-noise ratio in the associated light source/light detector pair baseline signal,
  (2) removing signal components from each baseline differential light source/light detector pair signal that correlate with other light source/light detector pair signals, and
  (3) removing signal components from each baseline differential light source/light detector pair signal that correlate with physiologic functions of the patient.

13. A method for detecting extravasation of a fluid applied to a patient according to claim 12 wherein the step of calculating a parameter-dependent extravasation volume includes:

(a) developing a sum signal that is the sum of the magnitudes of the new light source/light detector pair signals having an improved signal-to-noise ratio, and (b) multiplying the sum signal by a correction factor corresponding to an empirically determined parameter to correct for model inaccuracies.

14. A method for detecting extravasation of a fluid applied to a patient according to claim 12 wherein the step of calculating a parameter-dependent extravasation model includes:

(a) selecting separate coefficients for:
  (1) positive values of the new light source/light detector pair signals having an improved signal-to-noise ratio, and
  (2) negative values of the new light source/light detector pair signals having an improved signal-to-noise ratio, (b) multiplying:
  (1) positive new light source/light detector pair signals having an improved signal-to-noise ratio by the positive value coefficients, and
  (2) negative new light source/light detector pair signals having an improved signal-to-noise ratio by the negative value coefficients, (c) developing a sum signal of the new light source/light detector pair signals having an improved signal-to-noise ratio multiplied by the positive value coefficients and the new light source/light detector pair signals having an improved signal-to-noise ratio multiplied by the negative value coefficients, and (d) multiplying the sum signal by a correction factor corresponding to an empirically determined parameter to correct for model inaccuracies.

15. A method for detecting extravasation of a fluid applied to a patient according to claim 12 wherein:

(a) the tissue optical properties of the body part include absorption and scattering, and (b) the step of calculating a parameter-dependent extravasation model includes:
  (1) combining the new light source/light detector pair signals having an improved signal-to-noise ratio into a differential absorption image representative of the change in the spatially variant absorption from baseline,
  (2) combining the new light source/light detector pair signals having an improved signal-to-noise ratio into a differential scattering image representative of the change in the spatially variant scattering from baseline,
  (3) developing a sum absorption signal by performing a volume sum of the differential absorption image,
  (4) developing a sum scattering signal by performing a volume sum of the differential scattering image,
  (5) multiplying the sum absorption signal by a first correction factor corresponding to an empirically determined parameter to correct for model inaccuracies,
  (6) multiplying the sum scattering signal by a second correction factor corresponding to an empirically determined parameter to correct for model inaccuracies, and
  (7) adding the result of multiplying the sum absorption signal by a first correction factor corresponding to an empirically determined parameter to correct for model inaccuracies and the result of multiplying the sum scattering signal by a second correction factor corresponding to an empirically determined parameter to correct for model inaccuracies.

16. Extravasation detection apparatus comprising:

a support pad adapted for attachment to a body part of a patient in proximity to a site at which a fluid is to be injected into the patient;

at least one light source, mounted to said support pad, for radiating light into the body part;

means for energizing said light source in an encoded manner to radiate light into the body part in an encoded manner;

a plurality of light detectors, mounted to said support pad, for:
  (a) individually detecting light transmitted from said light source that is reflected, scattered, diffused or otherwise emitted from the body part, and
  (b) individually developing light source/light detector pair signals representative of the light detected individually by said light detectors;

means for developing, prior to injection of the fluid into the body part, a plurality of individual light source/light detector pair baseline signals associated with each light source/light detector pair and against which measurements made during injection of the fluid into the body part are compared;

means for comparing the light source/light detector pair signals with the associated light source/light detector pair baseline signals;

means for developing from the comparisons of the light source/light detector pair signals with the associated light source/light detector pair baseline signals new light source/light detector pair signals having an improved signal-to-noise ratio;

means for developing, prior to injection of the fluid into the body part, a model, dependent on the arrangement of said light source and said light detectors on said support pad, for calculating extravasation volume from the new light source/light detector pair signals having an improved signal-to-noise ratio;

means for combining, according to the extravasation model, the new light source/light detector signals having an improved signal-to-noise ratio to determine the volume of extravasation; and means for comparing the volume of extravasation with a prescribed level of extravasation.

17. Extravasation detection apparatus comprising:

a support pad adapted for attachment to a body part of a patient in proximity to a site at which a fluid is to be injected into the patient;

a plurality of light sources, mounted to said support pad, for radiating light into the body part;

means for energizing said light sources in an encoded manner to radiate light into the body part in an encoded manner;

at least one light detector, mounted to said support pad, for:
  (a) individually detecting light transmitted from said light sources that is reflected, scattered, diffused or otherwise emitted from the body part, and
  (b) individually developing light source/light detector pair signals representative of the light detected individually by said light detector;

means for developing, prior to injection of the fluid into the body part, a plurality of individual light source/light detector pair baseline signals associated with each light source/light detector pair and against which measurements made during injection of the fluid into the body part are compared;

means for comparing the light source/light detector pair signals with the associated light source/light detector pair baseline signals;

means for developing from the comparisons of the light source/light detector pair signals with the associated light source/light detector pair baseline signals new light source/light detector pair signals having an improved signal-to-noise ratio;

means for developing, prior to injection of the fluid into the body part, a model, dependent on the arrangement of said light sources and said light detector on said support pad, for calculating extravasation volume from the new light source/light detector pair signals having an improved signal-to-noise ratio;

means for combining, according to the extravasation model, the new light source/light detector signals having an improved signal-to-noise ratio to determine the volume of extravasation; and means for comparing the volume of extravasation with a prescribed level of extravasation.

* * * * *

UNITED STATES PATENT AND TRADEMARK OFFICE
CERTIFICATE OF CORRECTION

PATENT NO.   : 6,487,428 B1
DATED        : November 26, 2002
INVENTOR(S)  : Culver et al.

It is certified that error appears in the above-identified patent and that said Letters Patent is hereby corrected as shown below:

<u>Title page,</u>
Item [56], OTHER PUBLICATIONS, "O'Leary M.A.," reference, delete "diffusin" and insert -- diffusing --.
Item [57], ABSTRACT,
Line 18, delete "is".

<u>Column 16,</u>
Line 27, delete "he" and insert -- the --.
Line 28, delete "aid" and insert -- said --.

Signed and Sealed this

Fifteenth Day of July, 2003

JAMES E. ROGAN
*Director of the United States Patent and Trademark Office*